United States Patent
Zardi

(10) Patent No.: US 9,988,345 B2
(45) Date of Patent: Jun. 5, 2018

(54) PROCESS AND PLANT FOR THE PRODUCTION OF AN AQUEOUS SOLUTION COMPRISING UREA

(75) Inventor: Federico Zardi, Breganzona (CH)

(73) Assignee: Casale SA, Lugano (CH)

( * ) Notice: Subject to any disclaimer, the term of this patent is extended or adjusted under 35 U.S.C. 154(b) by 1208 days.

(21) Appl. No.: 12/525,655

(22) PCT Filed: Jan. 30, 2008

(86) PCT No.: PCT/EP2008/000698
§ 371 (c)(1),
(2), (4) Date: Feb. 10, 2010

(87) PCT Pub. No.: WO2008/092647
PCT Pub. Date: Aug. 7, 2008

(65) Prior Publication Data
US 2010/0140543 A1    Jun. 10, 2010

(30) Foreign Application Priority Data

Feb. 2, 2007    (EP) .................................. 07002265

(51) Int. Cl.
*C07C 273/00* (2006.01)
*C07C 273/16* (2006.01)

(52) U.S. Cl.
CPC .... *C07C 273/16* (2013.01); *B01D 2251/2062* (2013.01); *B01J 2219/00024* (2013.01); *Y10T 29/49826* (2015.01)

(58) Field of Classification Search
CPC .................................. C07C 273/16
USPC ........................................................ 252/184
See application file for complete search history.

(56) References Cited

U.S. PATENT DOCUMENTS

| 2,848,493 A | 8/1958 | Dewling et al. |
| 4,001,320 A * | 1/1977 | Kaasenbrood ........ C07C 273/04 564/66 |

FOREIGN PATENT DOCUMENTS

| EP | 0611753 A1 | 8/1994 |
| WO | 00/21881 A1 | 4/2000 |
| WO | 2006/096048 A1 | 9/2006 |
| WO | WO 2006096048 A1 * | 9/2006 ............. B01D 53/79 |

* cited by examiner

Primary Examiner — Michael Pepitone
(74) Attorney, Agent, or Firm — Akerman LLP

(57) ABSTRACT

The present invention regards a process for the production of an aqueous solution comprising urea for use in the removal of nitrogen oxides from combustion gas or fumes, the process being characterized in that it comprises the steps of: —subjecting at least a part of a urea-concentrated aqueous solution comprising residual free ammonia, obtained directly from or downstream of a recovery section of a plant for the production of urea, to washing with carbon dioxide, so obtaining a first vapor phase comprising carbon dioxide and optionally ammonia and a urea-concentrated aqueous solution comprising carbamate and essentially lacking in free ammonia, and —diluting said urea-concentrated aqueous solution comprising carbamate and essentially lacking in free ammonia with water until the desired concentration of urea in aqueous solution is reached.

11 Claims, 2 Drawing Sheets

PROCESS AND PLANT FOR THE PRODUCTION OF AN AQUEOUS SOLUTION COMPRISING UREA

CROSS-REFERENCE TO RELATED APPLICATIONS

This application is a national phase of PCT/EP2008/000698, filed Jan. 30, 2008, and claims priority to EP 07002265.2, filed Feb. 2, 2007, the entire contents of both of which are hereby incorporated by reference.

FIELD OF APPLICATION

The present invention refers, in its most general aspect, to a process for the production of an aqueous solution comprising urea intended for use in the removal of nitrogen oxides (Nox) present in combustion fumes, by means of their reduction with gaseous ammonia.

In particular, the present invention refers to a process of the aforesaid type in which the urea is obtained by synthesis starting from ammonia and carbon dioxide.

The present invention also regards a plant for the production of an aqueous solution comprising urea which implements a process of the aforesaid type.

PRIOR ART

As it is known, the international laws on the gaseous emissions deriving from the combustion of fossil fuels (combustion gas or fumes) impose in an increasingly strict manner the drastic reduction of the polluting substances contained in said gaseous emissions, including in particular the nitrogen oxides (Nox) since they are held responsible for the so-called acid rains.

For this purpose, different treatment processes of the gaseous emissions coming from the combustion of fossil fuels have been developed. In particular, the process of selective catalytic reduction of the nitrogen oxides (Nox)—better known as SCR—finds wide use, which permits eliminating a substantially large amount of NO and NO2 from the gaseous emissions, transforming them into compounds which are inert with regard to the environment, such as nitrogen and steam.

Such process is particularly employed for drastically reducing the nitrogen oxides from the gaseous emissions of heavy vehicles, in particular vehicles having diesel or turbo-diesel motors.

The SCR process is based on the following series of chemical reactions, which lead to the elimination of the nitrogen oxides by reaction with ammonia and oxygen contained in the current to be purified:

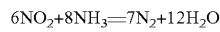

The above indicated reactions are all strongly exothermic, and it is estimated that on average a gaseous current containing 1000 ppm of NOx increases its temperature 10÷11° C. during the conversion process.

The optimal temperature interval for the SCR process is in the range of 180° C.-350° C. At temperatures lower than 180° C., the conversion is not complete and therefore it is not possible to ensure the generally required removal yields while at temperatures greater than 350° C. undesired reactions between ammonia and oxygen contained in the gaseous current occur such that at 400° C. about 5÷10% of ammonia is lost, mainly by means of the following reaction.

$$4NH_3 + 5O_2 = 4NO + 6H_2O \quad (4)$$

The presence of reactions antagonistic to those involved for the purification at temperatures greater than 350° C. and the practical need to not go below a minimum operating temperature of 200° C. makes the use of an appropriate catalytic system or catalyst indispensable for the actuation of the process; the latest generation heavy vehicles, such as for example the heavy vehicles with Euro 4 or Euro 5 motors, are normally equipped with such catalyst system or catalyst.

Regarding the feeding of ammonia necessary for the actuation of the SCR process, it is known to use ammonia or urea in an aqueous solution at a concentration normally in the range of 15-35% by weight on the weight of the solution.

Such aqueous solution is injected in the gaseous current to be purified upstream of the SCR catalytic system (or catalyst) by means of a pulveriser nozzle. Upstream of the catalytic system there may also be another static mixing device which ensures the necessary turbulence to the gaseous current, favouring the distribution of the reagent.

In particular, the use of urea in aqueous solution as reagent in the aforesaid process is very common since risks are avoided connected with the transportation or storage of the ammonia or its aqueous solutions. In this case, the ammonia necessary for the purification of the gaseous current to be treated is obtained from the decomposition of the urea in situ according to the following reaction:

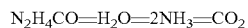

The decomposition reaction is endothermic and the necessary heat is provided by the gases to be treated (usually having a temperature greater than 300° C.), which also permits lowering the temperature of the gases to optimal values for the SCR process, as indicated above.

Regarding the obtainment of urea in aqueous solution for use in the removal of nitrogen oxides, the prior art first foresees the production of synthesis urea in melted form or granules by means of conventional urea plants and the subsequent dilution of the urea with water until the desired concentration of urea in the resulting aqueous solution is reached.

With such process, it is possible to obtain a final product (urea in aqueous solution) which is particularly pure and which is lacking in free ammonia—the ammonia being undesirable for its unpleasant odour and for its environmental impact—due to the fact that the synthesis urea (in melted form or granules) is obtained with a high purity (99% or greater purity).

Nevertheless, the aforesaid process involves a considerable energy consumption since in order to eliminate the ammonia through the obtainment of melted or granular urea with high purity it is necessary to concentrate a solution of urea obtained from the synthesis, so as to totally remove the solvent (water) from it, said solvent being then subsequently reintroduced in the dilution step of the melted or granular urea.

SUMMARY OF THE INVENTION

The technical problem underlying the present invention is therefore that of devising and making availably a process for the production of an aqueous solution comprising urea for use in the removal of nitrogen oxides from combustion gas or fumes starting from an aqueous solution of synthesis urea which overcomes the drawbacks mentioned with reference to the prior art, in particular a process of the aforesaid type in which it is possible to substantially remove the ammonia from said aqueous solution of synthesis urea at lower energy consumption with respect to the known processes.

Such technical problem is solved according to the invention by a process for the production of an aqueous solution comprising urea for use in the removal of nitrogen oxides from combustion gas or fumes, characterised in that it comprises the steps of:

- subjecting at least one part of a urea-concentrated aqueous solution comprising residual free ammonia, obtained directly from or downstream of a recovery section of a plant for the production of urea, to washing with carbon dioxide, with obtainment of a first vapour phase comprising carbon dioxide and optionally ammonia and a urea-concentrated aqueous solution comprising carbamate and essentially lacking in free ammonia,
- diluting said urea-concentrated aqueous solution comprising carbamate and essentially lacking in free ammonia with water until the desired concentration of urea in aqueous solution is reached.

Preferably, said desired concentration of urea in aqueous solution is in the range of 15-35% by weight on the weight of the solution.

According to a particularly preferred embodiment of the present invention, the urea-concentrated aqueous solution comprising residual free ammonia, to be subjected at least in part to washing with carbon dioxide, is obtained directly from the recovery section of a urea plant.

With the term "urea recovery section" it is intended that portion of the urea plant comprising per se conventional apparatuses for the treatment of aqueous solutions of urea obtained from the synthesis in order to reduce the content of carbamate and free ammonia present in such solutions. Such apparatuses comprise at least one dissociator or stripper for the carbamate which operates thermally or preferably by means of a stripping agent. Moreover, the recovery section usually has a pressure lower than that of the synthesis section in which urea is obtained from ammonia and carbon dioxide.

According to another preferred embodiment of the invention, the urea-concentrated aqueous comprising residual free ammonia, to be subjected at least in part to washing with carbon dioxide, comes from an evaporation section arranged downstream of said recovery section of the urea plant.

For this purpose, said urea-concentrated aqueous solution comprising residual free ammonia, to be subjected at least in part to washing with carbon dioxide, is preferably obtained from an evaporator of said evaporation section used to concentrate a urea-concentrated solution comprising residual free ammonia coming from the recovery section of the urea plant.

Thanks to the present invention, the urea-concentrated aqueous solution still comprising free ammonia obtained directly from or downstream of recovery section of a urea plant, is advantageously subjected, at least in part, to washing with carbon dioxide rather than subjected to evaporation as in the known processes mentioned above.

This leads to considerable advantages with respect to the prior art, including a considerably reduction of the energy consumption deriving from the smaller consumption of the washing with carbon dioxide with respect to those required by evaporation.

Moreover, the washing with carbon dioxide advantageously permits removing a substantially large amount of the free ammonia contained in said solution, converting it into the more innocuous carbamate (from the environmental impact standpoint) and possibly transporting it in part in vapour phase through a stripping action exerted by said carbon dioxide.

The urea-concentrated aqueous solution resulting from the washing with carbon dioxide is therefore essentially lacking in free ammonia and can be advantageously used in the removal of nitrogen oxides from the combustion fumes upon dilution of the same with water thus to have the right concentration of urea in aqueous solution (15-35% by weight on the weight of the solution) and an ammonia content below olfactory values, preferably below 150 ppm.

It should moreover be noted that the ammonium carbamate contained in the aforesaid aqueous solution of urea is advantageously decomposed together with the urea during the use of said solution in the removal of the Nox from the combustion fumes, so newly forming carbon dioxide and ammonia, the latter being available for the removal of the Nox.

The aforesaid technical problem is also solved by a plant for the production of an aqueous solution comprising urea for use in the removal of nitrogen oxides from combustion gas or fumes which implements the process of the invention described above.

In accordance with an embodiment of the invention, the plant comprises a urea synthesis section and a urea recovery section in fluid communication with each other, and is characterised in that it further comprises:

- a washing section with carbon dioxide arranged downstream of said recovery section of the urea,
- a feed duct arranged between said recovery section of the urea and said washing unit for feeding at least a part of a urea-concentrated aqueous solution comprising residual free ammonia obtained in said urea recovery section to said washing section,
- a feed duct of carbon dioxide to said washing section,
- a duct for the outlet of a urea-concentrated aqueous solution comprising carbamate and essentially lacking in free ammonia from said washing section, and
- a water feed duct in fluid communication with said outlet duct from the washing section, so to dilute said urea-concentrated aqueous solution comprising carbamate and essentially lacking free ammonia, until the desired concentration of urea in aqueous solution is obtained.

In accordance with another embodiment of the invention, the plant comprises a urea synthesis section, a urea recovery section and an evaporation section comprising a first evaporator and a second evaporator, said sections being in fluid communication with each other, and the plant is characterised in that it further comprises:

- a washing section with carbon dioxide arranged downstream of said urea recovery section,
- a feed duct arranged between said first evaporator and said washing unit for feeding at least a part of a urea-concentrated aqueous solution comprising residual free ammonia obtained in said first evaporator to said washing section,
- a feed duct of carbon dioxide to said washing section,
- a duct for the outlet of a urea-concentrated aqueous solution comprising carbamate and essentially lacking in free ammonia from said washing section, and
- a water feed duct in fluid communication with said outlet duct from the washing section in order to dilute said urea-concentrated aqueous solution comprising carbamate and essentially lacking in free ammonia in order to obtain the desired concentration of urea in aqueous solution.

The plant for the production of an aqueous solution comprising urea according to the present invention can be designed and manufactured ex-novo or preferably can be derived from a pre-existing plant for the production of synthesis urea.

In the latter case, in accordance with a further aspect of the present invention, a modernisation method (revamping) of a pre-existing plant is made available for the production of urea from ammonia and carbon dioxide of the type comprising a urea synthesis section and a urea recovery section in fluid communication with each other, which is characterised in that it comprises the steps of:
- arranging a washing section with carbon dioxide downstream of said urea recovery section,
- arranging a connection duct between said urea recovery section and said washing section for feeding at least a part of a urea-concentrated aqueous solution comprising residual free ammonia exiting from said urea recovery section to said washing section,
- arranging a feed duct of carbon dioxide to said washing section,
- arranging a duct for the outlet of a urea-concentrated solution comprising carbamate and essentially lacking in free ammonia from said washing section, and
- arranging a water feed duct in fluid communication with said outlet duct for diluting said urea-concentrated solution comprising carbamate and essentially lacking in free ammonia until the desired concentration of urea in aqueous solution is reached.

According to another embodiment of the invention, the modernisation method (revamping) of a pre-existing plant for the production of urea from ammonia and carbon dioxide of the type comprising a urea synthesis section, urea recovery section and an evaporation section comprising a first evaporator and a second evaporator, said sections being in fluid communication with each other, is characterised in that it comprises the steps of:
- arranging a washing section with carbon dioxide downstream of said urea recovery section,
- arranging a connection duct between said first evaporator and said washing unit for feeding at least a part of a urea-concentrated aqueous solution comprising residual free ammonia obtained in said first evaporator to said washing section,
- arranging a feed duct of carbon dioxide to said washing section,
- arranging a duct for the outlet of a urea-concentrated solution comprising carbamate and essentially lacking in free ammonia from said washing section, and
- prearranging a water feed duct in fluid communication with said outlet duct for diluting said urea-concentrated solution comprising carbamate and essentially lacking in free ammonia until the desired concentration of urea in aqueous solution is attained.

Further characteristics and advantages of the process for the production of urea in aqueous solution according to the present invention will be clear from the following description of a preferred embodiment thereof, given as indicative and non-limiting with reference to the attached drawings.

DETAILED DESCRIPTION OF A PREFERRED EMBODIMENT

Figure 1:
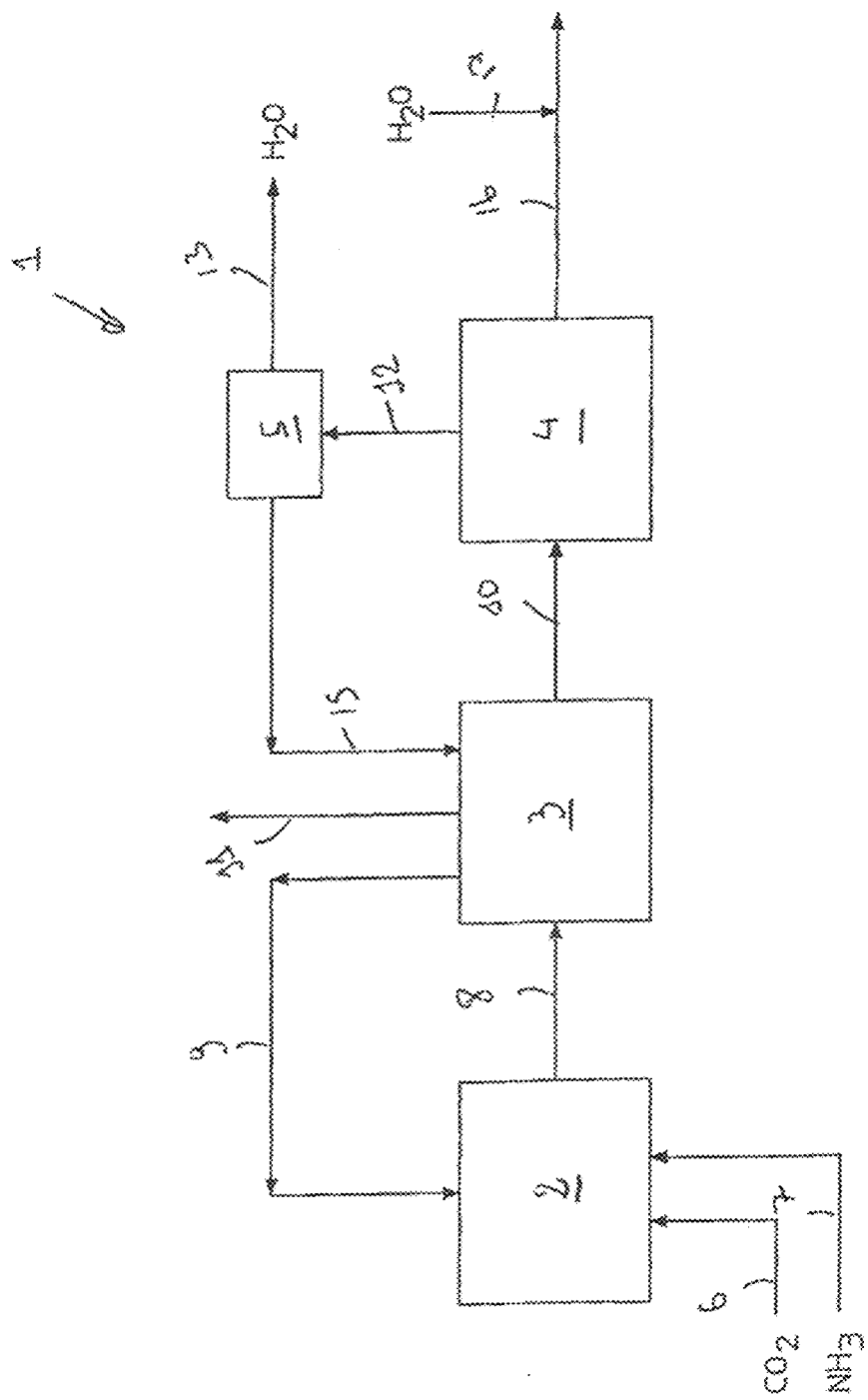
FIG. 1 represents a block diagram of a plant for the production of an aqueous solution comprising urea intended for use in the removal of nitrogen oxides from combustion fumes according to the prior art.

With reference to FIG. 1, a plant according to the prior art for the production of an aqueous solution comprising urea intended for use in the removal of nitrogen oxides from combustion fumes is indicated in its entirety with the reference number 1.

In the plant 1, the process for the production of urea in aqueous solution is based on the production of synthesis urea in the form of melted urea and on the subsequent dilution of the melted urea with water, until the desired concentration of urea is reached in the resulting aqueous solution.

More in particular, the plant 1 comprises a urea synthesis section 2 operating at a predetermined high pressure (for example 135-175 bars), a urea recovery section 3 operating at a predetermined low pressure (for example 1-10 bars), an evaporation section 4 and a treatment/condensation section 5 of the vapours obtained from the evaporation section 4, said sections being in fluid communication with each other.

The plant 1 moreover comprises ducts 6 and 7 for respectively feeding carbon dioxide and ammonia necessary for the urea synthesis in the synthesis section 2. In such section 2, the ammonia and carbon dioxide are made to react in an appropriate reactor, obtaining an aqueous solution comprising urea, ammonium carbamate and free ammonia which is fed to the urea recovery section 3 by means of a duct 8.

In the urea recovery section 3, the aforesaid solution comprising urea, ammonium carbamate and free ammonia is subjected to a decomposition treatment of the ammonium carbamate in suitable, per se conventional apparatuses, such as strippers, distillers, etc., with the obtainment of a vapour phase comprising ammonia and carbon dioxide, and a urea-concentrated solution (for example having a urea concentration equal to 70% by weight of the weight on the solution) and comprising residual free ammonia.

The vapour phase comprising ammonia and carbon dioxide exiting from the urea recovery section 3 is appropriately recycled to the synthesis section 2 by means of a duct 9 for further conversion to urea, while the urea-concentrated solution comprising residual free ammonia exiting from said recovery section 3 is fed to the evaporation section 4 by means of a duct 10.

More in particular, the aforesaid vapour phase comprising ammonia and carbon dioxide is recycled to the synthesis section preferably in condensate form (with the formation of a solution comprising ammonium carbamate) by means of a condensation liquid (usually a recycling carbamate solution) in a per se conventional condenser of the urea recovery section 3.

A gaseous flow comprising inert gases (for example nitrogen, hydrogen, oxygen etc.), usually present at the feeding of the carbon dioxide for protecting the reactor of the synthesis section 2 from corrosion, is also released from the urea recovery section 3, through a duct 11.

In the evaporation section 4, the aforesaid urea-concentrated solution comprising residual free ammonia is subjected to evaporation of the solvent (water) and removal of the residual free ammonia, by means of per se conventional apparatuses such as for example one or more evaporators etc., obtaining melted urea and a vapour phase comprising water and ammonia.

The vapour phase comprising water and ammonia exiting from the evaporation section 4 is appropriately fed by means of a duct 12 to the treatment section 5 which comprises a series of conventional apparatuses for the condensation of the same and the separation of residual gaseous components (mainly ammonia and carbon dioxide) from the water.

At the outlet of the treatment section 5, it is then obtained a liquid flow essentially composed of water, through a duct 13, for further use and a gaseous flow mainly composed of ammonia and carbon dioxide which is recycled to the urea recovery section 3 through a duct 15.

In the urea recovery section 3, the aforesaid gaseous flow composed mainly of ammonia can be subjected to conventional treatments and can be recycled preferably in condensate form to the synthesis section 2.

Instead, the melted urea obtained in the evaporation/distillation section 4 exits from said section 4 through a duct 16 and is mixed with water circulating in a duct 17 in fluid communication with the outlet duct 16 of the melted urea, thus obtaining a urea aqueous solution with the desired urea concentration, for example a concentration equal to 32% by weight on the weight of the solution.

Figure 2:
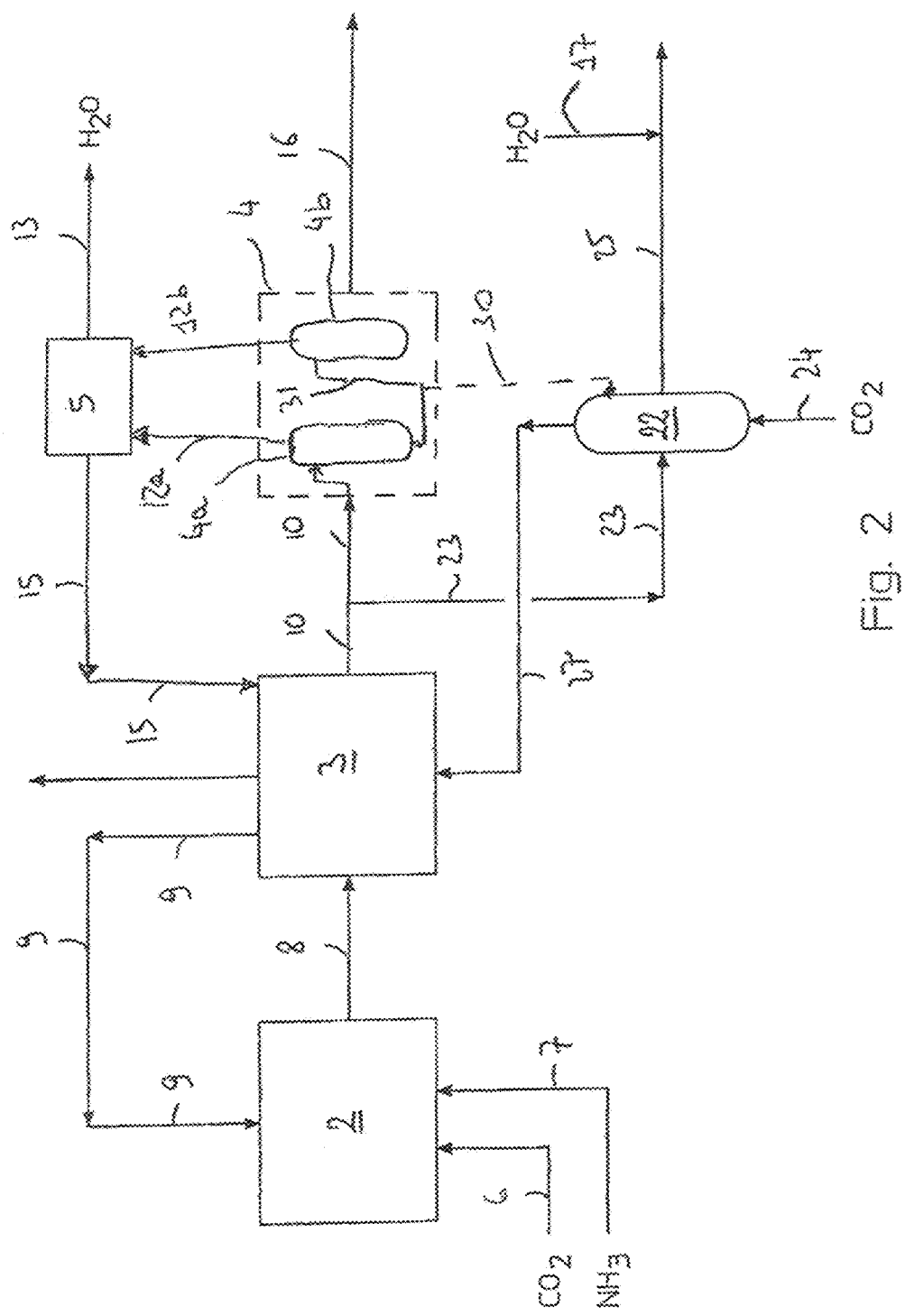
FIG. 2 represents a block diagram of a plant for the production of an aqueous solution comprising urea intended for use in the removal of nitrogen oxides from combustion fumes according to the present invention.

In FIG. 2 a plant is shown according to the invention for the production of urea in aqueous solution intended for use in the removal of nitrogen oxides from combustion fumes, the plant being entirely indicated with the reference number 20.

More in particular, the plant 20 according to the invention permits the production of synthesis urea and urea in aqueous solution suitable for use in the removal of nitrogen oxides from combustion fumes, as will be better explained below in the present description.

The same reference numbers will be attributed to the elements of plant 20 which are structurally or functionally equivalent to corresponding elements of the plant 1 described above. Furthermore such elements will not be described further for the sake of brevity.

The plant 20 comprises, like the plant 1 described above, a urea synthesis section 2 operating at a predetermined high pressure (for example 135-175 bars), a urea recovery section 3 operating at a predetermined low pressure (for example 1-10 bars), an evaporation section 4 and a treatment/condensation section 5 of the vapours obtained from the evaporation section 4, said sections being in fluid communication with each other.

More in particular, in the present example the evaporation section 4 comprises a first evaporator 4a and a second evaporator 4b arranged in series in fluid communication with each other and with the urea recovery section 3 (through the first evaporator 4a).

In accordance with the present invention, the plant 20 moreover comprises a washing unit 22 with carbon dioxide situated downstream of the urea recovery section 3 as well as a duct 23 arranged between the urea recovery section 3 and the washing section 22 for feeding a part of the urea-concentrated aqueous solution comprising residual free ammonia exiting from the urea recovery section 3 to said washing section 22.

More in particular, the duct 23 is in fluid communication with an outlet duct 10 of said urea-concentrated aqueous solution comprising residual free ammonia from the urea recovery section 3, by means of which the remaining part of said urea-concentrated aqueous solution comprising residual free ammonia is fed to the evaporation section 4.

In the washing section 22, the aforesaid urea-concentrated aqueous solution comprising residual free ammonia is subjected to washing with carbon dioxide, fed to the unit 22 through a suitable duct 24, which mainly leads to the conversion of the residual free ammonia contained in said solution to carbamate and the possible removal of part of the ammonia in vapour phase by means of a stripping action exerted by the carbon dioxide gaseous flow fed to the washing section 22.

For this purpose, the washing section 22 comprises one or more conventional apparatuses for exchange of mass between a liquid phase and a gaseous phase, such as for example, in particular, gas scrubbing apparatuses, plate distillation columns etc.

At the outlet of the washing unit 22, a urea-concentrated aqueous solution is therefore obtained comprising carbamate and substantially lacking in free ammonia as well as a vapour phase comprising carbon dioxide and optionally ammonia.

In accordance with the present invention, the urea-concentrated aqueous solution comprising carbamate and essentially lacking in free ammonia obtained in the washing section 22 is diluted with water circulating in a duct 17 in fluid communication with the outlet duct 25 of said solution from the washing section thus obtaining the desired urea concentration in aqueous solution, for example a concentration of urea equal to 30% by weight on the weight of the solution.

The vapour phase comprising carbon dioxide and optionally ammonia exiting from the washing section 22 is instead fed to the urea recovery section 3 for further per se conventional treatments, for example to allow it to be appropriately recycled to the synthesis section 2 preferably in condensate form, by means of a duct 27 arranged between the washing section 22 and the urea recovery section 3.

It should also be noted that, advantageously, the washing carbon dioxide fed to the washing section 22 can be a part of the feed carbon dioxide supplied to the urea synthesis section 2. Alternatively, the carbon dioxide can instead come from other parts of the plant of the invention or from external sources. Preferably, the washing carbon dioxide is fed to the section 22 in excess with respect to the ammonia content in the urea-concentrated solution, so as to convert substantially in a quantitative way said ammonia to carbamate.

It should moreover be noted that, in accordance with the present invention, the remaining part of the urea-concentrated aqueous solution comprising residual free ammonia exiting from the urea recovery section 3 and not sent to the washing section 22 is advantageously fed, through the duct 10, to the first evaporator 4a of the distillation section 4 and from this to the second evaporator 4b by means of the connection duct 31. From the first evaporator 4a a more urea-concentrated aqueous solution still comprising residual free ammonia is obtained, while in the second evaporator 4b the solvent is totally removed, so obtaining melted urea which exits from the evaporator 4b through the duct 16. From the evaporators 4a and 4b, respective vapour phases comprising water and ammonia are also obtained which are sent to the treatment in the section 5, as described above, by means of the respective ducts 12a and 12b.

In accordance with an embodiment of the invention (not shown in the figures), it can be foreseen to send the entire urea-concentrated aqueous solution comprising residual free ammonia to the washing section 22 with carbon dioxide, so as to attain only the production of aqueous solution comprising urea for the removal of NOxs. In this case, there is no need for the evaporation section 4 and the treatment section 5, or such sections can be done away with if pre-existing (for example in occasion of a revamping of the urea plant).

In accordance with another embodiment of the invention (shown with dashed line in FIG. 2), it can be foreseen to send a part of the urea-concentrated aqueous solution comprising residual free ammonia, exiting from the first evaporator 4a, to the washing section 22 by means of the connection duct 30. This can be done as an alternative to feeding to the washing section 22 the urea-concentrated aqueous solution comprising residual free ammonia exiting from the recovery section 3 or in addition to such supply.

The process and the plant according to the present invention therefore have a considerable flexibility of use, since it is possible to draw the aqueous solution comprising urea and residual ammonia to be sent to the washing in different and additional points of the plant, so as to satisfy specific and contingent needs.

Another advantage of the invention lies in the fact that, in the case of revamping pre-existing plants, the interventions to be carried out are minimal and do not require high costs, since it is necessary to simply prearrange a washing section and appropriate connection ducts between such section and the urea recovery section or the evaporation section of the pre-existing plant.

Of course, a man skilled in the art, for the purpose of satisfying specific and contingent needs, can make numerous modifications and variants to the above described process and plant for the production of an aqueous solution comprising urea, all moreover contained in the scope of protection of the present invention as defined by the following claims.

The invention claimed is:
1. A process for the production of an aqueous solution comprising urea for use in the removal of nitrogen oxides from combustion gas or fumes, comprising the steps of:
  obtaining a first urea-concentrated aqueous solution comprising residual free ammonia directly from or downstream of a recovery section of a plant for the production of urea;
  washing with carbon dioxide at least a part of said first urea-concentrated aqueous solution comprising residual free ammonia, thus converting an amount of said residual free ammonia into carbamate in the solution and obtaining a first vapour phase comprising carbon dioxide, and a second urea-concentrated aqueous solution comprising carbamate that is essentially lacking in free ammonia, and
  diluting said second urea-concentrated aqueous solution comprising carbamate and essentially lacking in free ammonia-with water until a desired concentration of urea in aqueous solution is reached.

2. The process according to claim 1, wherein said first urea-concentrated aqueous solution comprising residual free ammonia is obtained directly from a urea recovery section of a urea plant.

3. The process according to claim 1, wherein said first urea-concentrated aqueous solution comprising residual free ammonia comes from an evaporation section arranged downstream of said recovery section of the urea plant.

4. The process according to claim 3, wherein said first urea-concentrated aqueous solution comprising residual free ammonia is obtained from an evaporator of said evaporation section used to concentrate a urea-concentrated aqueous solution comprising residual free ammonia coming from said recovery section of the urea plant.

5. The process according to claim 1, wherein said desired concentration of urea in aqueous solution is in the range of 15%-35% by weight on the weight of the solution.

6. The process according to claim 1, comprising the step of subjecting an aqueous solution comprising urea, ammonium carbamate and free ammonia obtained in a synthesis section of the urea plant to decomposition of the ammonium carbamate, optionally in the presence of a stripping agent, in said urea recovery section, and obtaining a second vapour phase comprising ammonia and carbon dioxide and said first urea-concentrated aqueous solution comprising residual free ammonia.

7. The process according to claim 1, further comprising the step of feeding said first vapour phase comprising carbon dioxide to said urea recovery section.

8. The process according to claim 6, further comprising the step of recycling said second vapour phase comprising ammonia and carbon dioxide, in condensate form, to the urea synthesis section.

9. The process according to claim 1, comprising subjecting the entire said first urea-concentrated aqueous solution comprising residual free ammonia to washing with carbon dioxide.

10. The process according to claim 3, further comprising the step of subjecting a part of said first urea-concentrated aqueous solution comprising residual free ammonia not subjected to washing with carbon dioxide to evaporation in said evaporation section, so obtaining melted urea.

11. The process according to claim 1, wherein said first vapour phase containing carbon dioxide additionally contains an amount of ammonia.

* * * * *